(12) United States Patent
Mackerell, Jr. et al.

(10) Patent No.: US 10,002,228 B2
(45) Date of Patent: Jun. 19, 2018

(54) METHOD FOR BINDING SITE IDENTIFICATION BY MOLECULAR DYNAMICS SIMULATION (SILCS: SITE IDENTIFICATION BY LIGAND COMPETITIVE SATURATION)

(71) Applicant: University of Maryland, Baltimore, Baltimore, MD (US)

(72) Inventors: Alexander D. Mackerell, Jr., Baltimore, MD (US); Olgun Guvench, Portland, ME (US)

(73) Assignee: University of Maryland, Baltimore, Baltimore, MD (US)

( * ) Notice: Subject to any disclaimer, the term of this patent is extended or adjusted under 35 U.S.C. 154(b) by 397 days.

(21) Appl. No.: 14/945,792

(22) Filed: Nov. 19, 2015

(65) Prior Publication Data
US 2016/0070850 A1   Mar. 10, 2016

Related U.S. Application Data

(63) Continuation of application No. 13/265,568, filed as application No. PCT/US2010/032922 on Apr. 29, 2010, now abandoned.

(60) Provisional application No. 61/175,120, filed on May 4, 2009.

(51) Int. Cl.
| | |
|---|---|
| *G06F 19/12* | (2011.01) |
| *G06F 17/18* | (2006.01) |
| *G06F 19/16* | (2011.01) |
| *G06F 19/00* | (2018.01) |

(52) U.S. Cl.
CPC .............. *G06F 19/12* (2013.01); *G06F 17/18* (2013.01); *G06F 19/16* (2013.01); *G06F 19/706* (2013.01)

(58) Field of Classification Search
None
See application file for complete search history.

(56) References Cited

U.S. PATENT DOCUMENTS

| | | |
|---|---|---|
| 7,890,313 B2 | 2/2011 | Kite et al. |
| 2003/0187594 A1 | 10/2003 | Sherman et al. |

FOREIGN PATENT DOCUMENTS

| | | |
|---|---|---|
| EP | 1602646 A1 | 12/2005 |
| WO | 00/39751 A2 | 7/2000 |

OTHER PUBLICATIONS

Frembgen-Kesner T. et al., "Computational Sampling of a Cryptic Drug Binding Site in a Protein Receptor: Explicit Solvent Molecular Dynamics and Inhibitor Docking to p38 MAP Kinase", Journal of Molecular Biology, Academic Press, United Kingdom, vol. 359, No. 1, May 26, 2006 (May 26, 2006), pp. 202-214.

In 'T Veld P. J. et al., "Accurate and efficient methods for modeling colloidal mixtures in an explicit solvent using molecular dynamics", Computer Physics Communication, Elsevier Science Publishers B.V., Amsterdam, NL, vol. 179, No. 5, Sep. 1, 2008 (Sep. 1, 2008), pp. 320-329.

Ruscio J. Z. et al., "Atomic level computational identification of ligand migration pathways between solvent and binding site in myoglobin", Proceedings of the National Academy of Sciences, vol. 105, No. 27, Jul. 8, 2008 (Jul. 8, 2008), pp. 9204-9209.

Elmer S. P. et al., "Foldamer dynamics expressed via Markov state models. I. Explicit solvent molecular-dynamics simulations in acetonitrile, chloroform, methanol, and water", Journal of Chemical Physics, vol. 123, No. 11, Sep. 15, 2005 (Sep. 15, 2005), pp. 114902-1-14.

Jul. 6, 2016 Extended European Search Report issued in European Patent Application No. 10772603.6.

Abel, et al. Role of the active-site solvent in the thermodynamics of factor Xa ligand binding. J Am Chem Soc. Mar. 5, 2008;130(9):2817-31.

Carlson, et al. Developing a dynamic pharmacophore model for HIV-1 integrase. J Med Chem. Jun. 1, 2000;43(11):2100-14.

De Ruiter, et al. Efficient and accurate free energy calculations on trypsin inhibitors. Journal of Chemical Theory and Computation. 2012; 8:3686-3695.

Guvench, et al. Computational fragment-based binding site identification by ligand competitive saturation. PLoS Comput Biol. Jul. 2009;5(7).

Halperin et al. Proteins: Structure, Function, and Genetics 47:409-443,2002.

Kishan, K., Structural biology, protein conformations and drug designing. Curr Protein Pept Sci. Aug. 2007;8(4):376-80.

Landon et al. Identification of hot spots within druggable binding regions by computational solvent mapping of proteins. J Med Chem. Mar. 22, 2007;50(6):1231-40.

Miranker et al. Proteins: Structure, Function, and Genetics 1129-34, 1991.

Raman et al., Reproducing crystal binding modes of ligand functional groups using Site-Identification by Ligand Competitive Saturation (SILCS) simulations. J Chem Inf Model. Apr. 25, 2011;51(4):877-96.

Zhang et al. Solvent models for protein ligand binding: Comparison of implicit solvent poisson and surface generalized born models with explicit solvent simulations. Journal of Computational Chemistry. 2001; 22(6):591-607.

(Continued)

*Primary Examiner* — Michael Borin
(74) *Attorney, Agent, or Firm* — Mintz Levin Cohn Ferris Glovsky & Popeo, PC

(57) ABSTRACT

The invention describes an explicit solvent all-atom molecular dynamics methodology (SILCS: Site Identification by Ligand Competitive Saturation) that uses small aliphatic and aromatic molecules plus water molecules to map the affinity pattern of a large molecule for hydrophobic groups, aromatic groups, hydrogen bond donors, and hydrogen bond acceptors. By simultaneously incorporating ligands representative of all these functionalities, the method is an in silico free energy-based competition assay that generates three-dimensional probability maps of fragment binding (FragMaps) indicating favorable fragment:large molecule interactions. The FragMaps may be used to qualitatively inform the design of small-molecule ligands or as scoring grids for high-throughput in silico docking that incorporates both an atomic-level description of solvation and the large molecule's flexibility.

24 Claims, 11 Drawing Sheets

(56) References Cited

OTHER PUBLICATIONS

International Preliminary Report of Patentability, PCT/US2010/032922, dated Nov. 9, 2011.
International Search Report for International Application No. PCT/US2013/033200, dated Jul. 4, 2013.
International Search Report for International Application No. PCT/US2010/032922, dated Feb. 7, 2011.
Written Opinion of the International Searching Authority for International Application No. PCT/US2013/033200, dated Jul. 4, 2013.

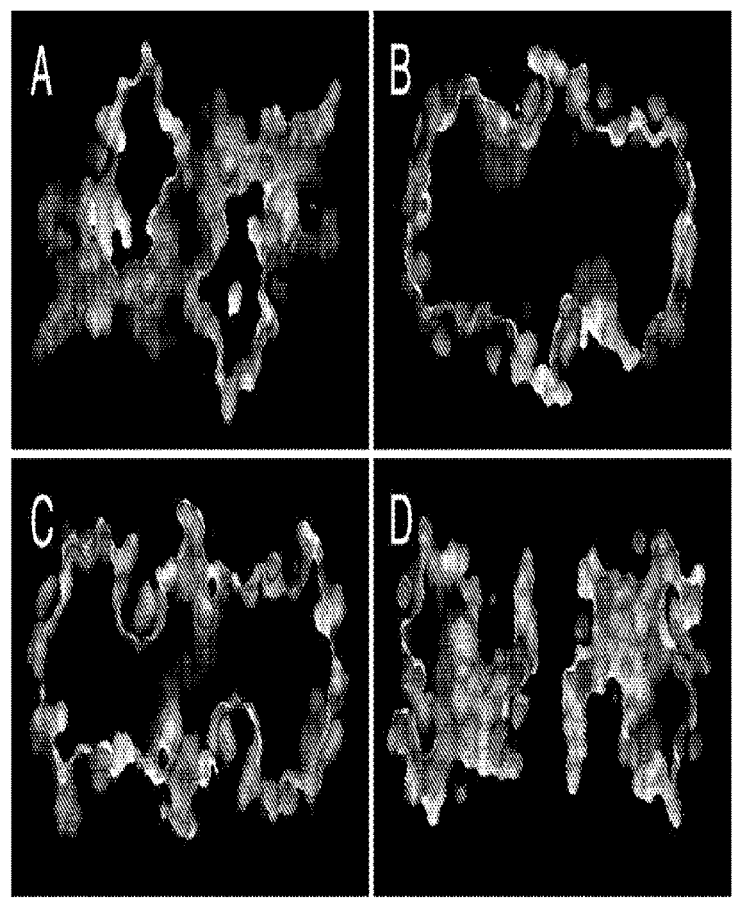
Figures 2A-D

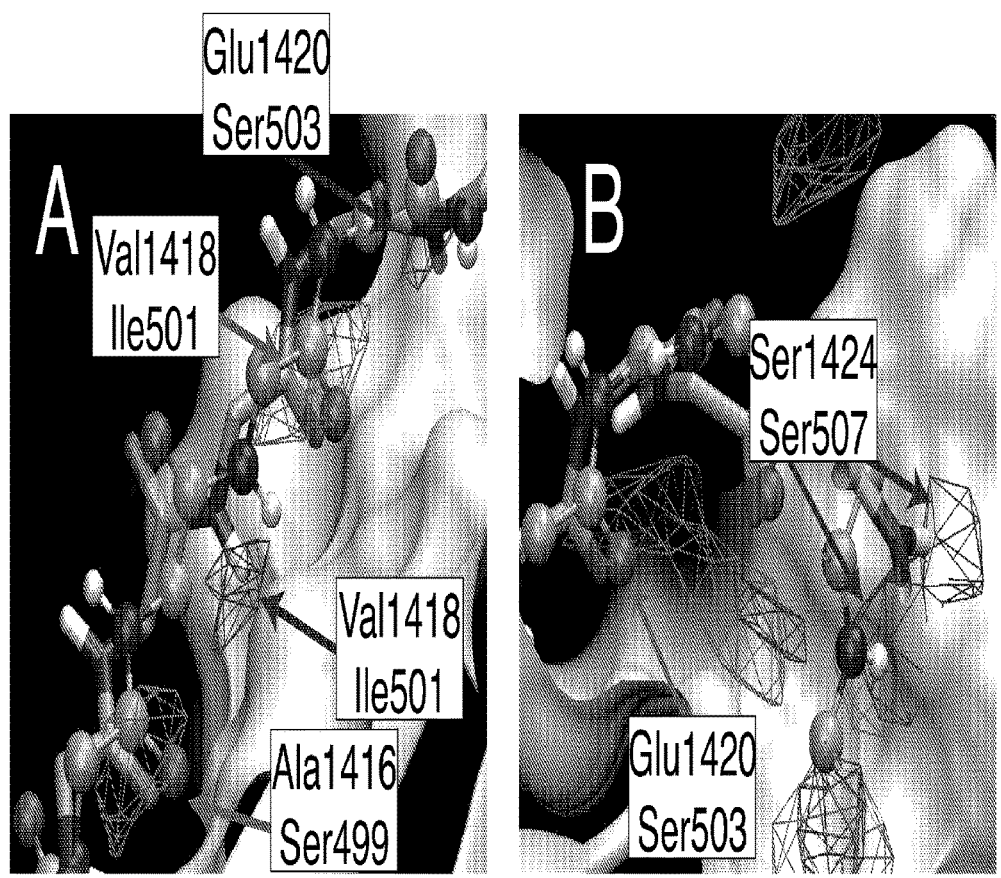
Figures 3A-B

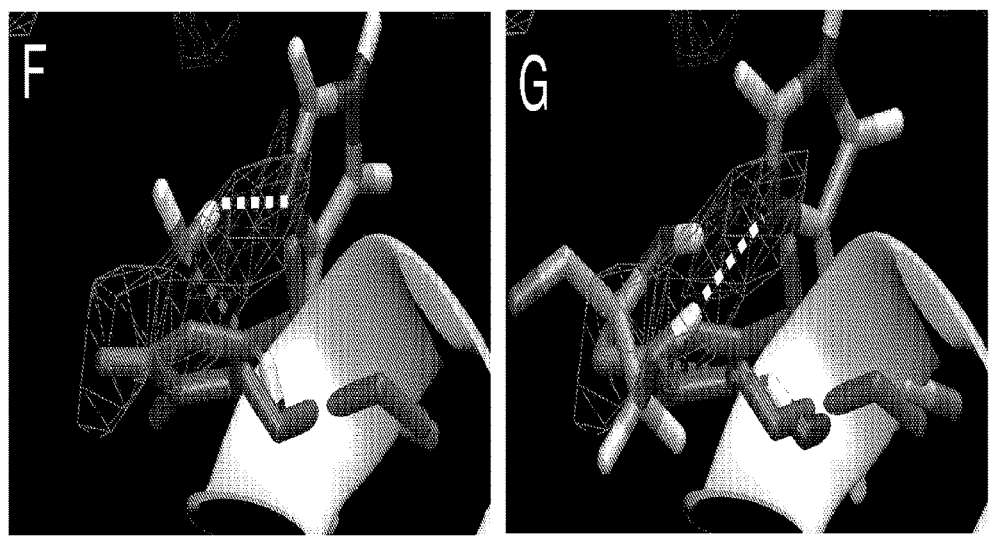
Figures 3F-G

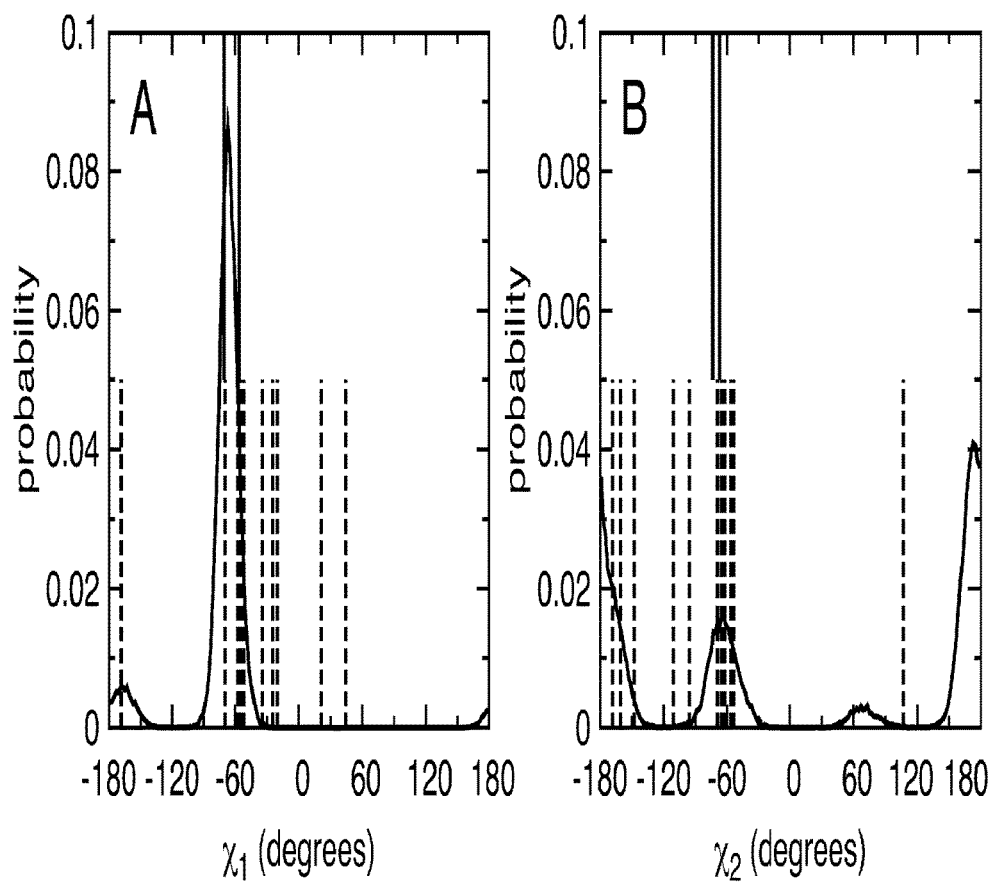
Figures 4A-B

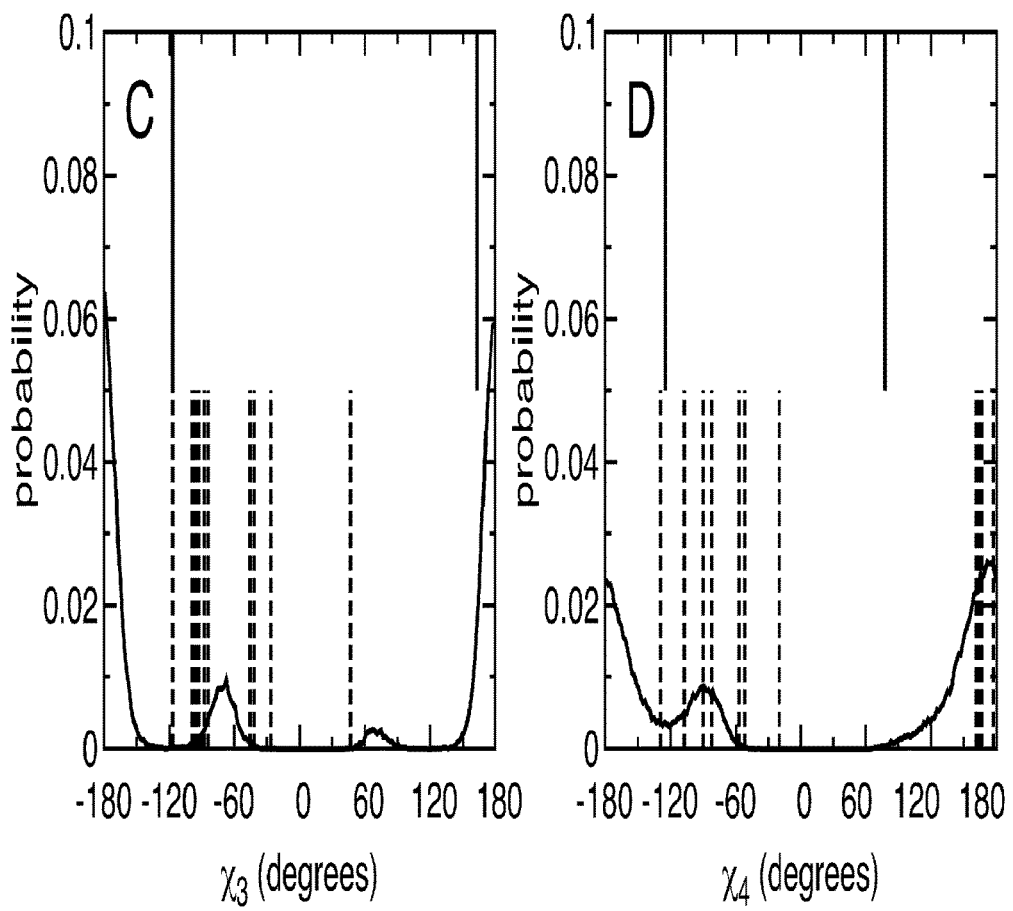
Figures 4C-D

METHOD FOR BINDING SITE IDENTIFICATION BY MOLECULAR DYNAMICS SIMULATION (SILCS: SITE IDENTIFICATION BY LIGAND COMPETITIVE SATURATION)

CROSS-REFERENCE TO RELATED APPLICATIONS

This application is a continuation of U.S. patent application Ser. No. 13/265,568 which entered the U.S. National Stage on Oct. 21, 2011, as a 371 application of PCT/US2010/032922 filed on Apr. 29, 2010, which claims the benefit of U.S. Provisional Application for Patent Ser. No. 61/175,120 filed on May 4, 2009, the contents of these applications being incorporated herein by reference in their entirety.

STATEMENT REGARDING FEDERALLY SPONSORED RESEARCH

This invention was made with government support under Grant Numbers GM051501, CA107331, CA120215 and CA119771 awarded by the National Institutes of Health. The government has certain rights in the invention.

BACKGROUND OF THE INVENTION

Field of the Invention

The present invention is directed to a method of computational chemistry for identifying binding sites by molecular dynamics simulations using ligand competitive saturation. In particular, the method overcomes the problem of small nonpolar molecule aggregation to allow competitive saturation in an aqueous solution at physiological conditions. More particularly, the method, when used in a two-tier approach, may determine which one of several multiple fragment molecules has a highest probability of improving binding to a surface region of a large molecule that is proximate to a bound ligand, in order to produce an optimized lead compound for drug discovery.

Description of the Related Art

Fragment-based drug discovery relies on a simple premise: identify small molecule fragments that bind to a target region of a large molecule and then evolve or link the small molecule fragments to create a larger high-affinity molecule. To a first approximation, the binding free-energies of fragments bound in non-overlapping poses are additive (Dill K A (1997) Additivity principles in biochemistry. *J Biol Chem* 272:701-704). Therefore, linking two such fragments with millimolar affinities, e.g., 4 kcal*mol$^{-1}$, will yield a single fragment molecule with a micromolar affinity of, e.g., 8 kcal*mol$^{-1}$, which is of sufficient affinity to serve as a "hit" for lead compound optimization in fragment-based drug discovery (Erlanson D A et al. (2004) Fragment-based drug discovery. *J Med Chem* 47:3463-3482). Since the 3-dimensional chemical space spanned by small fragments is orders of magnitude smaller than that spanned by molecules of sufficient size to be hits, it is feasible to screen a fragment library representative of the full extent of chemical space (Congreve M et al. (2008) Recent developments in fragment-based drug discovery. *J Med Chem* 51:3661-3680).

Nature imposes an upper limit on the contribution per ligand heavy atom to the binding free-energy (Kuntz I D et al. (1999) The maximal affinity of ligands. *Proc Natl Acad Sci USA* 96:9997-10002), commonly referred to as ligand efficiency, (LE) (Hopkins A L et al. (2004) Ligand efficiency: a useful metric for lead selection. *Drug Discov Today* 9:430-431). This limit means that even the best fragments, having an LE value of 0.4-0.5 kcal*mol$^{-1}$ per heavy atom, still have weak affinities for their target regions, making their screening by traditional assays difficult. Consequently, fragment-based drug discovery relies on sensitive biophysical methods to detect fragment binding.

Among these biophysical methods are NMR spectroscopy and x-ray crystallography. These two methods additionally yield 3-dimensional structural information about fragment binding poses, which is useful for confirming that two fragments indeed bind to two adjacent sites and can be productively linked. However, despite the utility of NMR spectroscopy and x-ray crystallography to detect fragment binding, there are significant time, labor, and materials costs associated with these two biophysical fragment-based drug discovery approaches.

Computational approaches to fragment-based drug discovery can mitigate the costs of experimental fragment-based drug discovery based on such biophysical techniques as, NMR spectroscopy and x-ray crystallography. Currently, in computational approaches, the large molecule is assumed to be rigid and fragments populate the surface of the, for example, rigid protein molecule using an energy function that models the solvent environment as a continuum (Miranker A, et al. (1991) Functionality maps of binding-sites—a multiple copy simultaneous search method. *Proteins: Struct, Funct, Genet* 11:29-34; Carlson H A, et al. (2000) Developing a dynamic pharmacophore model for HIV-1 integrase. *J Med Chem* 43:2100-2114; Landon M R, et al. (2007) Identification of hot spots within druggable binding regions by computational solvent mapping of proteins. *J Med Chem* 50:1231-1240). As a result, these computational approaches are limited in their ability to accurately account for the exemplary protein molecule's conformational heterogeneity and solvation effects, contributions that are essential to compute free energies of binding of small molecules to the target region of the exemplary protein molecule (Guvench O, et al. (2009) Computational evaluation of protein-small molecule binding. *Curr Opin Struct Biol* 19:56-61).

In reality, protein molecules can accommodate ligands by undergoing conformational changes (Arkin M R, et al. (2004) Small-molecule inhibitors of protein-protein interactions: Progressing towards the dream. *Nat Rev Drug Discovery* 3:301-317), and water plays an important role in protein:ligand binding affinity (Lu Y P, et al, (2006) Binding free energy contributions of interfacial waters in HIV-1 protease/inhibitor complexes. *J Am Chem Soc* 128:11830-11839; Young T, et al. (2007) Motifs for molecular recognition exploiting hydrophobic enclosure in protein-ligand binding *Proc Natl Acad Sci USA* 104:808-813). Significant recent advances have been made with regard to both incorporating protein flexibility, for example by screening against multiple different rigid protein conformations (Bowman A L, et al. (2007) Small molecule inhibitors of the MDM2-p53 interaction discovered by ensemble-based receptor models. *J Am Chem Soc* 129:12809-12814; Amaro R E, et al. (2008) An improved relaxed complex scheme for receptor flexibility in computer-aided drug design. *J. Comput-Aided. Mol. Des.* 22:693-705; Totrov M, et al. (2008) Flexible ligand docking to multiple receptor conformations: a practical alternative. *Curr Opin Struct Biol* 18:178-184), and more accurate modeling of solvation effects in energy functions (Abel R, Young T, Farid R, Berne B J, Friesner R A (2008) Role of the active-site solvent in the thermodynamics of Factor Xa ligand binding. *J Am Chem Soc* 130:2817-2831).

Nonetheless, approximations used in computational approaches to date still limit the accuracy of fragment placement and fragment scoring, which relates to affinity of the fragment for the binding site, and, ultimately, the determination of the most suitable fragment for a selected binding-site region of the protein molecule.

All-atom explicit-solvent molecular dynamics (MD) simulations of proteins give an atomic-level-of-detail description of the motions of both a large biomolecule, for example, a protein, and water atoms at relevant temperature and pressure (Karplus M, et al. (2002) Molecular dynamics simulations of biomolecules. *Nat Struct Biol* 9:646-652). In this case, the MD computational simulation samples a Boltzmann distribution of thermally accessible protein conformations, and with the ability of the MD simulation to reach the nanosecond timescale, the sampled conformations include changes in sidechain dihedral angles as well as loop motions of the protein.

Furthermore, MD simulation-based methods are able to rigorously determine the absolute binding free energy of a ligand to a protein molecule (Woo H J, et al. (2005) Calculation of absolute protein-ligand binding free energy from computer simulations. *Proc Natl Acad Sci USA* 102: 6825-6830; Deng Y Q, et al. (2006) Calculation of standard binding free energies: Aromatic molecules in the T4 lysozyme L99A mutant. *J Chem Theory Comput* 2:1255-1273; Wang J, et al. (2006) Absolute binding free energy calculations using molecular dynamics simulations with restraining potentials. *Biophys J* 91:2798-2814; Jiao D, et al. (2008) Calculation of protein-ligand binding free energy by using a polarizable potential. *Proc Natl Acad Sci USA* 105:6290-6295; Lee M S, et al. (2006) Calculation of absolute protein-ligand binding affinity using path and end-point approaches. *Biophys J* 90:864-877; Lee M S, et al. (2008) Calculation of absolute ligand binding free energy to a ribosome-targeting protein as a function of solvent model. *J Phys Chem B* 112:13411-13417). However, such MD simulated free-energy calculations are computationally expensive, limiting MD simulations from being used directly for high-throughput in silico screening.

There remains a need for a method of computational chemistry that identifies the binding sites of small molecules and small molecule fragments to a large molecule while (1) mitigating the costs of NMR spectroscopy and x-ray crystallography of experimental fragment-based drug discovery and (2) including detailed representations of both a large molecule's conformational heterogeneity and solvation effects.

SUMMARY OF THE INVENTION

Toward overcoming present costs and limitations of fragment-based computational drug design, the inventors describe a method that combines ideas from experimental fragment-based drug discovery, using NMR and crystallographic methods, with all-atom explicit-solvent MD simulations, using small aliphatic and aromatic molecules plus water molecules to map the affinity pattern for hydrophobic groups, aromatic groups, hydrogen bond donors, and hydrogen bond acceptors to a large molecule. The method, SILCS: Site Identification by Ligand Competitive Saturation, involves computationally "immersing" a large molecule, e.g., a protein, a glycoprotein, DNA, RNA, a carbohydrate, or a glycolipid, in an aqueous solution containing different types of small molecules having concentrations sufficient for competitive saturation, such that convergence of the simulation is anticipated. The large molecule+small molecules+ water system is then subjected to multiple MD simulations allowing for competitive binding of the small molecules to the large molecule. Snapshots from the multiple MD simulation trajectories are combined to generate 3-dimensional (3D) probability maps, i.e., FragMaps, which reveal what molecular functionalities, e.g., aliphatic molecules, aromatic molecules, hydrogen bond donor molecules, and hydrogen bond acceptor molecules, bind most strongly to different parts of the large molecule's surface. Because the SILCS FragMaps are generated from MD simulations, they incorporate both the large molecule's flexibility with a Boltzmann distribution of conformations, as well as atomic-level solvation effects, resulting in 3D SILCS FragMaps that represent rigorous free energy distributions. Notably, the invention of the present method requires minimal time, labor, and materials compared to the conventional experimental approaches.

The SILCS FragMaps of the invention, when visualized as isosurfaces in conjunction with, for example, a large protein molecule (please see, for example, FIGS. 3A-G) may be used to guide the development of, for example, an inhibitor ligand, at a particular site on the exemplary large protein molecule's surface. The FragMaps may contain information about the exemplary protein's flexibility and atomically-detailed solvation effects as they impact fragment binding. Additionally, the relative importance of interactions is represented by the values of histogram counts, which may correspond to a high-probability of fragment binding, in the 3D FragMap histograms. Thus, in an exemplary embodiment of the invention, an inhibitor ligand may be optimally designed by targeting overlap of the inhibitor ligand with high-probability regions of fragment binding in the FragMaps. In an exemplary embodiment of the invention, this may be done in an automated, quantitative manner by taking the natural logarithm of the probabilities and multiplying by $-RT$, where R is the Boltzmann constant and T the temperature, and subsequently using the resultant free-energy maps as docking grids for high-throughput in silico docking of drug-like compound libraries. The use of SILCS free-energy FragMaps as docking grids offers significant improvement over current high-throughput in silico methods, which are limited in their descriptions of a large molecule's, for example, a protein's, a glycoprotein's, DNA's, RNA's, a carbohydrate's, or a glycolipid's, flexibility and solvation.

The SILCS method of the invention may also be used in a two-tier approach that optimizes design of lead compounds in drug-discovery. A first tier of the approach may use the SILCS method to identify binding sites for molecular functionalities on a large molecule adjacent to which a fragment ligand is bound. A second tier of the approach may then use the identities of these functional binding sites to select specific small molecules, i.e., fragments, which may be assayed by a second SILCS simulation for lead compound optimization.

For example, if the first SILCS assay identified a region of the large molecule, adjacent to the lead compound, to which a hydrogen bond donor and an aromatic molecule were bound, then the second SILCS assay may simulate the small molecule binding of a molecule, which contains both hydrogen bond donor and aromatic functionalities, for example, imidazole, phenol, aniline, pyridine, and pyrrole. In an exemplary embodiment of the invention, each of these dual-functionality molecules would be added to the system of a corresponding MD simulation of the large molecule to which the lead compound is bound, and the resulting probability distributions for each of these dual-functionality molecules would then be used to identify that dual-functionality molecule that has the most favorable position adjacent to the lead compound to improve binding. This particular dual-functionality molecule, which is most likely to improve binding, may then be chemically linked to the lead compound to provide an improved lead compound for drug-discovery.

Additionally, an important part of the SILCS method of the invention is its computational feasibility. In an exemplary embodiment of the invention, each 5-ns SILCS simulation of an exemplary BCL-6 oncoprotein took less than three days on a single 2×4-core node of a commodity-computing cluster, and because each of the ten simulations was independent, they were all run simultaneously to yield converged FragMaps in under three days. The ability to achieve converged FragMaps probability maps in such a short time is a very important result, since MD simulations are often limited by the computational cost for simulations beyond the nanosecond regime, which in turn limits their utility in computer-aided drug discovery.

In view of the foregoing, an embodiment of the invention provides for a method of computational chemistry for identifying binding sites, by molecular dynamics (MD) simulations using ligand competitive saturation. The method includes: inputting a 3-dimensional (3D) structure of a protein; preparing multiple solutions for ligand competitive saturation, each of the multiple solutions corresponding to a volumetric grid in which either a benzene, a propane, or a water molecule is randomly placed on a grid point, such that, a spacing of the grid points and the random placing of the benzene, propane, or water molecules corresponds to a concentration sufficient for competitive saturation of the benzene and propane molecules; overlaying the 3D structure of the protein with each of the multiple solutions and removing all benzene, propane and water molecules that overlay the protein in the volumetric grid; introducing a repulsive interaction energy between the benzene and the propane molecules to prevent non-polar aggregation; minimizing energies and equilibrating each of the multiple solutions with the protein by MD simulations to produce multiple equilibrated systems; propagating MD simulations for each of the multiple equilibrated systems; binning atoms from each of the propagated MD simulations into voxels, in which benzene and propane carbon atoms are binned as aromatic and aliphatic carbons, respectively, and in which water oxygen and hydrogen atoms are binned as hydrogen bond acceptors and hydrogen bond donors, respectively; using bin counts for each of the aromatic and aliphatic carbons, and the hydrogen bond acceptors and hydrogen bond donors, based on their free energies of binding from the propagated MD simulations, to identify surface regions of the protein having a high probability to bind one of an aromatic carbon atom, an aliphatic carbon atom, a hydrogen bond acceptor oxygen atom, and a hydrogen bond donor hydrogen atom; and using the identified surface regions of the protein as docking grids for high-throughput in silico docking of drug-like compounds.

Another embodiment of the method of the invention further includes assigning an orientation of each of His, Gln, and Asn sidechains to the 3D structure of the protein.

Yet another embodiment of the method of the invention further includes aligning the protein from a trajectory of the propagated MD simulations.

Yet another embodiment of the method of the invention further includes introducing harmonic positional restraints to all atoms of the protein before equilibrating the multiple systems, and subsequently replacing the harmonic positional restraints with weak restraints on protein backbone carbon atoms to prevent denaturation before propagating the MD simulations.

Yet another embodiment of the method of the invention further includes creating fragment binding maps (FragMaps) of the surface regions of the protein, each of the FragMaps corresponding to the high probability of binding one of an aromatic carbon atom, an aliphatic carbon atom, a hydrogen bond acceptor oxygen atom, and a hydrogen bond donor hydrogen atom, wherein the FragMap represents a single isocontour value, empirically chosen, to optimize visualization of each of the FragMaps.

Yet another embodiment of the invention provides the method in which the protein is a glycoprotein.

Yet another embodiment of the invention provides the method in which the concentration sufficient for competitive saturation of the benzene and propane molecules is 1 M benzene and 1 M propane.

Yet another embodiment of the invention provides the method in which the concentration sufficient for competitive saturation of the benzene and propane molecules is greater than 0.01 mM and less than 10 M benzene and greater than 0.01 mM and less than 10 M propane.

Yet another embodiment of the invention provides for a method of computational chemistry for identifying binding sites, by molecular dynamics (MD) simulations using ligand competitive saturation. The method includes: inputting a 3-dimensional (3D) structure of a large molecule, in which the large molecule comprises one of DNA, RNA, a carbohydrate and a glycolipid; preparing multiple solutions for ligand competitive saturation, each of the multiple solutions corresponding to a volumetric grid in which either a small aromatic molecule, a small aliphatic molecule, or a water molecule is randomly placed on a grid point, such that, a spacing of the grid points and the random placing of small aromatic molecules, small aliphatic molecules, or water molecules corresponds to a concentration sufficient for competitive saturation of the small aromatic molecules and the small aliphatic molecules; overlaying the 3D structure of the large molecule with each of the multiple solutions and removing all the small aromatic molecules, the small aliphatic molecules, and the water molecules that overlay the large molecule in the volumetric grid; introducing a repulsive interaction energy between the small aromatic molecules and the small aliphatic molecules to prevent non-polar aggregation; minimizing energies and equilibrating each of the multiple solutions with the large molecule by MD simulations to produce multiple equilibrated systems; propagating MD simulations for each of the multiple equilibrated systems; binning atoms from each of the propagated MD simulations into voxels, in which carbon atoms of the small aromatic molecules and the small aliphatic molecules are binned as aromatic and aliphatic carbons, respectively, and in which water oxygen and hydrogen atoms are binned as hydrogen bond acceptors and hydrogen bond donors, respectively; using bin counts for each of the aromatic and aliphatic carbons, and the hydrogen bond acceptors and hydrogen bond donors, based on their free energies of binding from the propagated MD simulations, to identify surface regions of the large molecule having a high probability to bind one of an aromatic carbon atom, an aliphatic carbon atom, a hydrogen bond acceptor oxygen atom, and a hydrogen bond donor hydrogen atom; and using the identified surface regions of the large molecule as docking grids for high-throughput in silico docking of drug-like compounds.

Yet another embodiment of the invention provides for a method of computational chemistry for identifying binding sites, by molecular dynamics (MD) simulations using ligand competitive saturation, for drug design optimization. The method includes: inputting a 3-dimensional (3D) structure of a complex of a protein and a bound ligand; preparing multiple solutions for ligand competitive saturation, each of the multiple solutions corresponding to a volumetric grid in which either a benzene, a propane, or a water molecule is randomly placed on a grid point, such that, a spacing of the grid points and the random placing of the benzene, propane, or water molecules corresponds to a concentration sufficient for competitive saturation of the benzene and propane molecules; overlaying the 3D structure of the protein and the bound ligand with each of the multiple solutions and removing all benzene, propane and water molecules that overlay the protein and the bound ligand in the volumetric grid; introducing a repulsive interaction energy between the benzene and the propane molecules to prevent non-polar aggregation; minimizing energies and equilibrating each of the multiple solutions with the protein and the bound ligand by MD simulations to produce multiple equilibrated systems; propagating a first tier of MD simulations for each of the multiple equilibrated systems; binning atoms from each of the propagated MD simulations into voxels, wherein benzene and propane carbon atoms are binned as aromatic and aliphatic carbons, respectively, and wherein water oxygen and hydrogen atoms are binned as hydrogen bond acceptors and hydrogen bond donors, respectively; using bin counts for each of the aromatic and aliphatic carbons, and the hydrogen bond acceptors and hydrogen bond donors, based on their free energies of binding, from the first tier of propagated MD simulations to identify surface regions of the protein having a high probability to bind one of an aromatic carbon atom, an aliphatic carbon atom, a hydrogen bond acceptor oxygen atom, and a hydrogen bond donor hydrogen atom; identifying a surface region of the protein that is proximate to the bound ligand and has a high probability of binding to at least two of an aromatic carbon atom, an aliphatic carbon atom, a hydrogen bond acceptor oxygen atom, and a hydrogen bond donor hydrogen atom; selecting multiple fragment molecules, containing the at least two of an aromatic carbon atom, an aliphatic carbon atom, a hydrogen bond acceptor oxygen atom, and a hydrogen bond donor hydrogen atom, for a second tier of MD simulations; preparing multiple solutions for ligand competitive saturation of the selected multiple fragment molecules; introducing an intermolecular repulsive interaction energy between nonpolar regions of the selected multiple fragment molecules to prevent non-polar aggregation; minimizing energies and equilibrating each of the multiple solutions with the protein and the bound ligand by MD simulations to produce multiple equilibrated systems; propagating the second tier of MD simulations for each of the multiple equilibrated systems; and analyzing the second tier of MD simulations to determine which one of the selected multiple fragment molecules has a highest probability of improving binding to the surface region of the protein that is proximate to the bound ligand.

Yet another embodiment of the method of the invention further includes chemically linking one of the selected multiple fragment molecules, having a highest probability of improving binding to the surface region of the protein that is proximate to the bound ligand, to the bound ligand to design an optimized drug.

Yet another embodiment of the method of the invention further includes assigning an orientation of each of His, Gln, and Asn sidechains to the 3D structure of the protein.

Yet another embodiment of the method of the invention further includes aligning the protein from a trajectory of the first and second tier propagated MD simulations.

Yet another embodiment of the method of the invention further includes introducing harmonic positional restraints to all atoms of the protein before equilibrating the multiple systems in the first and second tier MD simulations, and subsequently replacing the harmonic positional restraints with weak restraints on protein backbone carbon atoms to prevent denaturation before propagating the first and second tier MD simulations.

Yet another embodiment of the invention provides the method in which the multiple fragment molecules comprise any of methanol, phenol, imidazole, aniline, pyridine, pyrrole, and acetone.

Yet another embodiment of the invention provides the method in which the protein is a glycoprotein.

Yet another embodiment of the invention provides the method in which the concentration sufficient for competitive saturation of the multiple fragment molecules is 1 M.

Yet another embodiment of the invention provides the method in which the concentration sufficient for competitive saturation of the fragment molecules is greater than 0.01 mM and less than 10 M.

Yet another embodiment of the invention provides the method in which analysis of the second tier of MD simulations is based on binning atoms of the selected multiple fragment molecules from each of the propagated MD simulations into voxels for each of the multiple equilibrated systems.

Yet another embodiment of the invention provides for a method of computational chemistry for identifying binding sites, by molecular dynamics (MD) simulations using ligand competitive saturation, for drug design optimization. The method includes: inputting a 3-dimensional (3D) structure of a complex of a large molecule and a bound ligand, in which the large molecule comprises one of DNA, RNA, a carbohydrate and a glycolipid; preparing multiple solutions for ligand competitive saturation, each of the multiple solutions corresponding to a volumetric grid in which either a benzene, a propane, or a water molecule is randomly placed on a grid point, such that, a spacing of the grid points and the random placing of the benzene, propane, or water molecules corresponds to a concentration sufficient for competitive saturation of the benzene and propane molecules; overlaying the 3D structure of the large molecule and the bound ligand with each of the multiple solutions and removing all benzene, propane and water molecules that overlay the large molecule and the bound ligand in the volumetric grid; introducing a repulsive interaction energy between the benzene and the propane molecules to prevent non-polar aggregation; minimizing energies and equilibrating each of the multiple solutions with the large molecule and the bound ligand by MD simulations to produce multiple equilibrated systems; propagating a first tier of MD simulations for each of the multiple equilibrated systems; binning atoms from each of the propagated MD simulations into voxels, in which benzene and propane carbon atoms are binned as aromatic and aliphatic carbons, respectively, and in which water oxygen and hydrogen atoms are binned as hydrogen bond acceptors and hydrogen bond donors, respectively; using bin counts for each of the aromatic and aliphatic carbons, and the hydrogen bond acceptors and hydrogen bond donors, based on their free energies of binding, from the first tier of propagated MD simulations to identify surface regions of the large molecule having a high probability to bind one of an aromatic carbon atom, an aliphatic carbon atom, a hydrogen bond acceptor oxygen atom, and a hydrogen bond donor hydrogen atom; identifying a surface region of the large molecule that is proximate to the bound ligand and has a high probability of binding to at least two of an aromatic carbon atom, an aliphatic carbon atom, a hydrogen bond acceptor oxygen atom, and a hydrogen bond donor hydrogen atom; selecting multiple fragment molecules, containing the at least two of an aromatic carbon atom, an aliphatic carbon atom, a hydrogen bond acceptor oxygen atom, and a hydrogen bond donor hydrogen atom, for a second tier of MD simulations; preparing multiple solutions for ligand competitive saturation of the selected multiple fragment molecules; introducing an intermolecular repulsive interaction energy between nonpolar regions of the selected multiple fragment molecules to prevent non-polar aggregation; minimizing energies and equilibrating each of the multiple solutions with the large molecule and the bound ligand by MD simulations to produce multiple equilibrated systems; propagating the second tier of MD simulations for each of the multiple equilibrated systems; and analyzing the second tier of MD simulations to determine which one of the selected multiple fragment molecules has a highest probability of improving binding to the surface region of the large molecule that is proximate to the bound ligand.

BRIEF DESCRIPTION OF THE DRAWINGS

The embodiments of the invention will be better understood from the following detailed description with references to the drawings, in which:

FIGS. 2A-D illustrate successive slices of the aliphatic carbon atom FragMap, generated by mapping propane carbon atoms, and the BCL-6 molecular surface taken perpendicular to the two-fold symmetry axis of the protein, according to an embodiment of the invention;

FIGS. 3A-G illustrate SILCS FragMaps for BCL-6, where: FIGS. 3A-C show hydrogen bond donor (blue mesh) and hydrogen bond acceptor (red mesh) SILCS FragMaps isosurfaces overlapping with the N-terminal (FIG. 3A), the central (FIG. 3B), and the C-terminal residues (FIG. 3C) in the SMRT and BCOR peptides, in which SMRT peptide atoms are represented as balls-and-sticks and BCOR atoms as tubes, and the BCL-6 molecular surface from the BCL-6:SMRT complex is also shown; FIGS. 3D-E show SILCS FragMaps for BCL-6 overlapping with the C-terminal residues of the SMRT and BCOR peptides, in which the molecular surface of the BCL-6 protein from the BCL-6:SMRT cocrystal is white, high-probability isosurfaces from the FragMaps are represented as meshes, with the aliphatic carbon FragMap in green, the aromatic carbon in purple, the hydrogen bond donor in blue, and hydrogen bond acceptor in red, and in which thermodynamically important residues in FIG. 3D, the SMRT peptide, and FIG. 3E, the BCOR peptide, are shown as sticks, and the residue/FragMap overlaps are labeled; FIGS. F-G show conformations of BCL-6 His116 in the BCL-6:SMRT cocrystal in purple, sampled during SILCS MD (colored by atom type), and in the BCL-6:BCOR cocrystal (colored by atom type), in which FIG. 3F shows the BCL-6:SMRT cocrystal His116 conformation used to seed the simulations overlaid with a SILCS MD snapshot of the His116 conformation having an interacting water molecule, and FIG. 3G shows the BCL-6:SMRT cocrystal His116 conformation overlaid with the BCL-6:BCOR cocrystal His116 conformation and BCOR Ser508, and in which the hydrogen bond donor FragMap is shown as a blue isocontour mesh, the hydrogen bond acceptor FragMap as a red isocontour mesh, and the helix containing His116 is represented as a white ribbon in FIGS. 3F-G, according to an embodiment of the invention;

FIGS. 4A-D illustrate Arg24 sidechain (A) $\chi_1$, (B) $\chi_2$, (C) $\chi_3$, and (D) $\chi_4$ dihedral distributions from the SILCS MD simulations, in which the starting dihedral values from BCL-6 in the BCL-6:SMRT complex [PDB ID 1R2B] are shown as solid lines, and the dihedral values in unliganded BCL-6 [PDB ID 1R28, 1R29] and in the BCL-6:BCOR [PDB ID 3BIM] complex are shown as dashed lines, according to an embodiment of the invention;

DETAILED DESCRIPTION OF PREFERRED EMBODIMENTS OF THE INVENTION

Figure 1A:
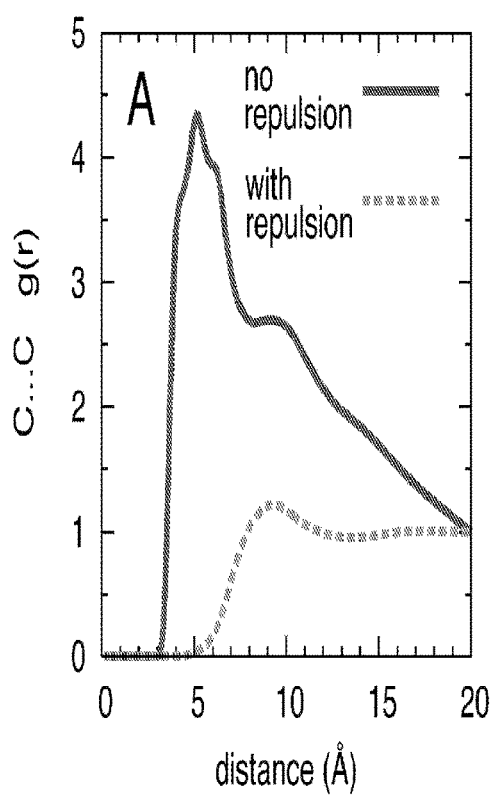
FIG. 1A illustrates computed simulations of carbon . . . carbon (C . . . C) radial distribution functions g(r) for an aqueous solution containing 1M propane and 1M benzene without and with a repulsive intermolecular interaction, according to an embodiment of the invention.

The embodiments of the invention and the various features and advantageous details thereof are explained more fully with reference to the non-limiting embodiments of that are illustrated in the accompanying drawings and detailed in the following description. It should be noted that the features illustrated in the drawings are not necessarily drawn to scale. Descriptions of well-known materials, components, and processing techniques are omitted so as to not unnecessarily obscure the embodiments of the invention. The examples used herein are intended to merely facilitate an understanding of ways in which the embodiments of the invention may be practiced and to further enable those of skill in the art to practice the embodiments of the invention. Accordingly, the examples should not be construed as limiting the scope of the embodiments of the invention.

As stated above, there remains a need for a method of computational chemistry that identifies the binding site of fragments to a molecule which mitigates the costs of NMR spectroscopy and x-ray crystallography in experimental fragment-based drug discovery and that overcomes the limited treatment of a large molecule's conformational heterogeneity and solvation effects in existing computational methods.

In the following exemplary embodiment of the invention, 3D probability maps, i.e., Site Identification by Ligand Competitive Saturation (SILCS) FragMaps, were generated to reveal what types of small molecule functionalities bound most strongly to regions in a large molecule, in this example, the BTB domain of the BCL-6 oncoprotein (Ahmad K F, et al. (2003) Mechanism of SMRT corepressor recruitment by the BCL6 BTB domain. *Mol Cell* 12:1551-1564; Ghetu A F, et al. (2008) Structure of a BCOR corepressor peptide in complex with the BCL6 BTB domain dimer. *Mol Cell* 29:384-391). The SILCS FragMaps generated from the MD simulations, initiated from the BCL-6:SMRT cocrystal conformation, predicted the pattern of aliphatic, aromatic, hydrogen bond donor, and hydrogen bond acceptor interactions seen in both the BCL-6:SMRT and BCL-6:BCOR 3-dimensional cocrystal structures, which bound the SMRT and the BCOR corepressors, respectively. Thus, the predictive MD simulations of the present invention replicated the molecular solvation effects and the free-energy criteria indicated by the binding patterns of the two corepressors to the BCL-6 protein in the cocrystals. Furthermore, the MD simulations also sampled the sidechain conformation for His116 as seen in the BCL-6:BCOR cocrystal, a conformation that is required for hydrogen bonding with BCOR Ser508 and which is significantly different from that of the SMRT-bound BCL-6 MD initial conformation, emphasizing the ability of the present invention to replicate the protein flexibility indicated by the two different sidechain conformations associated with the binding of the two different corepressors.

Methods:

The Site Identification by Ligand Competitive Saturation (SILCS) methodology may include: computationally "immersing" a large molecule, to which a fragment ligand is bound, in an aqueous solution of different small molecules, in which each of the different small molecules corresponds to a particular fragment type and each of the small molecule concentrations is sufficient for a competitive saturation assay, e.g., 0.01 mM≤[small molecule]≤10 M); running multiple nanosecond-length MD simulations of the composite large molecule+small molecules+water system; computing probability maps for each of the different small molecules' binding and the binding of water functionalities, i.e., hydrogen bond donor and hydrogen bond acceptor, to the large molecule for each of the multiple simulations; and combining probability maps of the same small molecule and water molecule functionalities from each of the multiple simulations to generate a single probability map, i.e., a SILCS FragMap, corresponding to an affinity for each of the different small molecules and the water functionalities. Once generated, the SILCS FragMaps for each small molecule, corresponding to a fragment type, and for each water functionality may be used to qualitatively inform the assembly of a lead compound for drug-discovery, based on a fragment library, or as docking grids for high-throughput in silico screening. Two important aspects of the SILCS methodology include the choice of small molecule types and overcoming small molecule aggregation.

Choice of Small Molecules:

The majority of moieties on drug-like molecules that may target a large molecule, for example, a protein, a glycoprotein, DNA, RNA, a carbohydrate, and a glycolipid, fall into four functional classes: aliphatic, aromatic, hydrogen bond donor, and hydrogen bond acceptor. This reflects the relatively limited chemical diversity of the amino acid sidechains of a protein, of the nucleotides of DNA and RNA, and of the carbon-carbon, carbon-hydrogen, carbon-oxygen, oxygen-phosphate and oxygen-hydrogen bonds of carbohydrates and glycolipids. Salt bridges between two amino acids in a protein or a glycoprotein, may, for example, be considered as a special case of hydrogen bonding, since the interaction is never directly between two charged heavy atoms but between a negatively-charged oxygen and a proton on a positively-charged nitrogen. Fragment libraries generated from existing drugs and drug-like molecules reflect this limited diversity, largely comprising hydrogen bond donors of amides, hydrogen bond acceptors of carbonyls and ethers, hydrophobic groups of small-length aliphatic chains, and aromatic/cyclic groups of benzene (Kolb P, et al. (2006) Automatic and efficient decomposition of two-dimensional structures of small molecules for fragment-based high-throughput docking. *J Med Chem* 49:7384-7392).

A first goal in the choice of small molecules for use in the inventive method of SILCS was to minimize the set of fragments, so as to be able to maximize their individual concentrations, which in turn maximizes binding for a competitive saturation assay and helps computational convergence on the MD simulation's timescale. To this end, the inventors selected a minimalist small-molecule set that contained hydrophobic aliphatic moieties, aromatic moieties, hydrogen bond donors, and hydrogen bond acceptors. Propane was chosen to represent hydrophobic aliphatic groups because propane's termini are small enough to fit into cavities only large enough to accommodate a methyl group, while the propane molecule itself is large enough to disrupt the hydrogen bonding structure of water so as to induce strong hydrophobic binding (Huang D M, et al. (2000) Temperature and length scale dependence of hydrophobic effects and their possible implications for protein folding. *Proc Natl Acad Sci USA* 97:8324-8327). Additionally, unlike longer-chain alkanes, propane is essentially a rigid body, excepting the rotation of the two terminal methyl groups, and thus computational convergence of internal degrees of freedom is not an issue. The inventors selected benzene to represent aromatic groups as benzene occurs in over 40% of drug-like compounds and is four times more common than the next most-common aromatic moiety (Kolb P, et al. (2006) Automatic and efficient decomposition of two-dimensional structures of small molecules for fragment-based high-throughput docking. *J Med Chem* 49:7384-7392). Finally, water was selected as a small molecule that contains both hydrogen bond donating and accepting capabilities and that mimics physiological conditions. Water is at a concentration of 55 M in solution and also has no internal conformational degrees of freedom, again promoting computational convergence on the MD timescale. Other small-molecule possibilities for hydrogen bond donors and acceptors may include acetone, formaldehyde, small amides, and related molecules.

A second goal in a choice of small molecules for use in the inventive method of SILCS was to minimize their molecular sizes, to maximize convergence, both by facilitating reversible binding on the MD simulation's timescale and allowing for fast diffusion through the bulk solvent. Even with a high-ligand efficiency, i.e. 0.4 kcal*mol$^{-1}$ per heavy atom, fragments consisting of 3-6 heavy atoms will have binding affinities of only 1.2 to 2.4 kcal*mol$^{-1}$ (100 millimolar to 10 millimolar). While such weak binding affinity can be a liability in an experimental NMR or x-ray crystallography approach, as it may push the limits of detection, it is an asset in the SILCS approach, allowing for ligand exchange from a binding site on the MD simulation's timescale; thus, facilitating the implementation of a competitive saturation in silico binding assay.

Another benefit of small fragment molecules, having only 3-6 heavy atoms, is their high diffusion rate that leads to quick mixing and rapid translation in the solution to different regions of the large molecule surface. Thus, small fragment molecules of minimal molecular size are beneficial both because of rapid binding exchange with the large molecule and rapid diffusion around the large molecule. However, it should be emphasized that the SILCS approach may be amenable to a wide selection of fragment-like small molecules and competitive saturation concentrations of the selected small molecules, and that the small molecules selected for the present example, i.e., benzene, propane, and water, were chosen for computational expediency of the exemplary embodiments.

Overcoming Small-Molecule Aggregation:

To ensure binding of small low-affinity molecules, a concentration sufficient to ensure competitive saturation of each small molecule was used in the MD simulations. However, a simulation of a solution of, for example, 1M propane and 1M benzene in water, would be prone to severe hydrophobic aggregation, as seen in the intermolecular carbon . . . carbon (C . . . C) radial distribution function, g(r), of FIG. 1A, which traces the relative probability of observing this pair of atoms at a given separation distance. Referring to FIG. 1A, the simulated carbon . . . carbon radial distribution function, g(r), for an aqueous solution containing 1M propane and 1M benzene has a large peak at 5 Å, associated with the distance between carbons in two fragments that are in direct contact, i.e., aggregated. This trace slowly decays with increasing distance, reflecting the fact that for a hydrophobic aggregation in water, it is much more likely to have two hydrophobic fragments adjacent to each other than at a larger separation. Such aggregation drastically reduces the effective concentration of hydrophobic fragments, which in turn hampers their sampling of the large molecule's surface and prevents SILCS FragMap computational convergence.

Because the inventive method of SILCS is a computational approach, it is possible to modify the interactions between hydrophobic/aromatic fragments to prevent small molecule aggregation. This was done by introducing a repulsive interaction energy between the hydrophobic/aromatic fragments, which comes into effect only when two such fragments come closer than a given interaction distance. This repulsive interaction energy was applied to selected fragment:fragment interactions in the exemplary system, i.e., propane-propane, benzene-benzene, and propane-benzene pairs, while all fragment:water, fragment:large molecule, water:water, water:large molecule, and large molecule:large molecule interactions remained unperturbed. This repulsive interaction energy stops nonpolar aggregation of hydrophobic/aromatic fragments but does not effect interactions of the nonpolar ligands with water or the large molecule. In essence, application of the repulsive interaction energy to small nonpolar molecules achieves ideal solution behavior in a solution having competitive saturation of the small nonpolar molecules, which is computationally necessary for convergence of the system. This repulsive interaction was implemented using the Lennard-Jones term (Allen, M P, et al., (1987) *Computer Simulation of Liquids*, Oxford University Press, Oxford, pp. _____) by adding an additional massless particle to the geometric center of each selected aromatic small molecule, for example, benzene, and the central carbon of each selected hydrophobic small molecule, for example, propane. These massless particles served as interaction sites for the inter-fragment repulsive interaction energy between nonpolar hydrophobic/aromatic fragments.

Figure 1B:
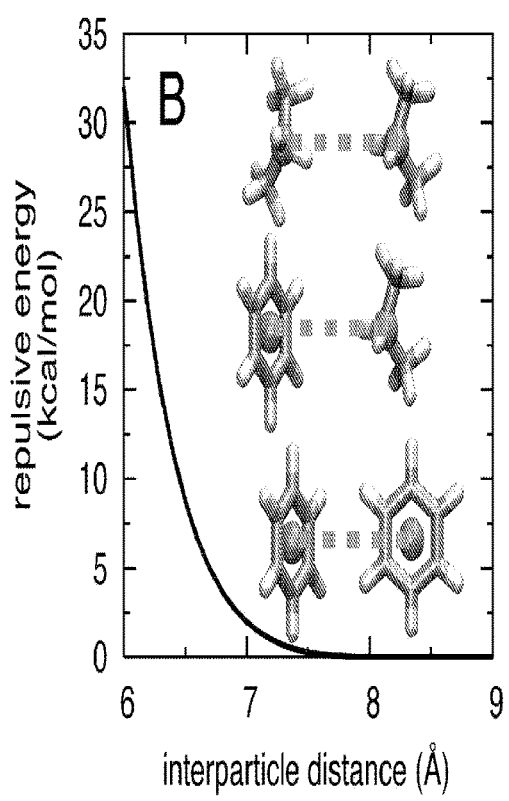
FIG. 1B illustrates the location of repulsive interaction energy sites on propane and benzene molecules (spheres), and the repulsive interaction energy profile between two repulsive interaction energy sites, according to an embodiment of the invention.

As illustrated in FIG. 1B, Lennard-Jones parameters, combined with a switching function operating between 5 Å and 8 Å, yield an energy vs. distance profile that is purely repulsive. With this additional repulsive interaction energy in effect, even at very high concentrations, the small nonpolar molecules will not aggregate. Thus, in the exemplary computational simulation of 1M propane and 1M benzene in water, the g(r) contact peak at 5 Å disappears, indicating the lack of direct intermolecular C . . . C contacts, while the flat g(r) trace at larger distances indicates a homogeneous distribution of the small molecules in solution, as shown in FIG. 1A with repulsive interaction energy in effect.

SILCS MD Simulations:

An exemplary embodiment of the invention used the experimentally-derived BCL-6 protein conformation from the BCL-6:SMRT complex to seed all SILCS MD simulations. The Reduce software (Word J M, et al. (1999) Asparagine and glutamine: Using hydrogen atom contacts in the choice of side-chain amide orientation. *J Mol Biol* 285: 1735-1747; kinemage.biochem.duke.edu/software/reduce.php) was used to place missing hydrogen positions, including assignment of protonation states, and to choose optimal Asn and Gln sidechain amide and His sidechain ring orientations. In this exemplary embodiment, the small hydrophobic molecule, propane, and the small aromatic molecule, benzene, were placed on a square grid, with the identity of the small molecule at each grid point randomly determined Ten such grids were generated with the grid spacing selected to yield a concentration of 1M propane and 1M benzene when combined with a box of water molecules at the experimental density of water. Ten protein+small molecules+water systems were generated by overlaying the coordinates of the experimentally-derived BCL-6 protein conformation and water molecules from the BCL-6:SMRT co-crystal structure with each of the ten solutions, then removing all water, propane, and benzene molecules that overlapped the target BCL-6 protein, and finally replacing two random water molecules with chloride ions to give a net neutral system charge. The final systems were rectangular boxes of 72×58×43 Å, which accommodated the BCL-6 protein with maximum dimensions of 64×48×35 Å.

In an exemplary embodiment of the invention, harmonic positional restraints with a force constant of 1 kcal*mol$^{-1}$*Å$^{-2}$ were placed on all protein atoms and the system was minimized for 500 steps with a steepest descent algorithm. Molecular dynamics (MD) simulations were performed on each minimized system using the "leap frog" version of the Verlet integrator with a 2-fs timestep to propagate the system. The SHAKE algorithm (Ryckaert J P, et al. (1977) Numerical integration of Cartesian equations of motion of a system with constraints: molecular dynamics of n-alkanes. *J Comput Phys* 23:327-341) was applied to constrain bonds to hydrogen atoms to their equilibrium lengths and maintain rigid water geometries; long-range electrostatic interactions were handled with the particle-mesh Ewald method with a real-space cutoff of 8 Å, a switching function was applied to Lennard-Jones interactions in the range of 5 to 8 Å, and a long-range isotropic correction was applied to the pressure for Lennard-Jones interactions beyond the 8 Å cutoff length. With the harmonic positional restraints still in place, the system was heated to 298 K over 20 ps by periodic reassignment of velocities, followed by 20 ps of equilibration at 298 K, also using velocity reassignment. Alternatively, the MD simulations may be done without the harmonic positional restraints, if the protein molecule is aligned in accordance with the trajectories of the MD simulations.

After the heating and equilibration periods, the harmonic positional restraints were replaced by weak restraints on only protein backbone C$_\alpha$ positions with a very weak force constant of 0.01 kcal*mol$^{-1}$*Å$^{-2}$ so as to prevent possible denaturation of the protein. These weak restraints on the protein backbone atoms allowed for significant protein flexibility, while preventing possible protein denaturation during the subsequent SILCS MD simulations. It is possible that in some cases, these weak restraints may not be necessary to prevent denaturation. Alternatively, the MD simulations may be done without the weak restraints, if the protein molecule is aligned in accordance with the trajectories of the MD simulations.

In an exemplary embodiment of the invention, each system was subsequently simulated for 5 nanoseconds at 298 K and 1 atm, with the Nose-Hoover thermostat and the Langevin piston barostat, for a total of 50 nanoseconds of simulation time. All simulations were done with the CHARMM molecular simulation software (Brooks B R, et al. (1983) CHARMM: a program for macromolecular energy, minimization, and dynamics calculations. *J Comput Chem* 4:187-217), the CHARMM protein force field (MacKerell A D, Jr., et al. (1998) All-atom empirical potential for molecular modeling and dynamics studies of proteins. *J Phys Chem B* 102:3586-3616) with CMAP backbone correction (MacKerell A D, Jr., et al. (2004) Extending the treatment of backbone energetics in protein force fields: Limitations of gas-phase quantum mechanics in reproducing protein conformational distributions in molecular dynamics simulations. *J Comput Chem* 25:1400-1415), and the TIP3P water model (Jorgensen W L, et al. (1983) Comparison of simple potential functions for simulating liquid water. *J Chem Phys* 79:926-935) modified for the CHARMM force field (Durell S R, et al. (1994) Solvent-induced forces between two hydrophilic groups. *J Phys Chem* 98:2198-2202).

Fragmap Construction:

In an exemplary embodiment of the invention, FragMaps were prepared for each SILCS simulation by binning atoms from SILCS MD snapshots taken at 2-ps intervals into 1 Å×1 Å×1 Å cubic volume elements, i.e., voxels, of a grid spanning the entire system in an exemplary embodiment of the invention. For the aliphatic and aromatic carbon FragMaps, carbon atoms for propane and benzene molecules, respectively, were binned if they were within 5 Å of the protein. For the hydrogen bond donor and acceptor FragMaps, water hydrogen and oxygen atoms, respectively, were binned if they were within 2.5 Å of the protein. For each type of FragMap, the respective FragMaps from each of the ten simulations were added together to create a single FragMap. A single isocontour value resulting in optimal visualization was empirically chosen for each FragMap type, and this value was used to generate all isocontour molecular graphics for that FragMap type. The ratio of the isocontour value to the average cubic volume element occupancy in an equilibrated system consisting of only propane, benzene, and water molecules was 9.8 for propane carbons, 9.8 for benzene carbons, 1.3 for water hydrogens, and 1.1 for water oxygens. Visualization of FragMaps and preparation of molecular graphics were done with VMD (Humphrey W, et al. (1996) VMD: Visual molecular dynamics. *J Mol Graph* 14:33-38.

Experimental Results and Discussion:

The BTB domain of the BCL-6 protein was chosen as an exemplary embodiment of the inventive SILCS method because of several favorable properties. The first is that the BCL-6 protein has two-fold symmetry, with two identical symmetry-related binding sites, allowing for measuring convergence of fragment sampling by analyzing the two-fold symmetry in the SILCS FragMaps. A second reason is that the binding of native ligands to the two binding sites shows no cooperativity; thus, the binding sites are independent of each other and the occupancy of one site will not affect the occupancy of the other. A third reason is that two known ligands for BCL-6, SMRT and BCOR, are peptides 17 amino-acids in length that bind in extended conformations to the same groove over a large contact-area, allowing for comparison of FragMaps over a large portion of the protein. Fourth, there is thermodynamic data available from competition assays using single-residue alanine or glycine-substituted analogs of these two peptides for every position in each peptide. Fifth, SMRT and BCOR have different binding modes in the BCL-6 peptide-binding cleft and lack sequence similarity. The different binding modes include BCL-6 sidechains in the binding cleft assuming different conformations in the presence of SMRT vs. BCOR. And finally, BCL-6 has clinical importance because of its association with diffuse large B-cell lymphoma, and competitive inhibitors that bind to the BCL-6 peptide-binding cleft may have therapeutic applications.

Convergence is Achievable in the Md Timescale:

In an exemplary embodiment of the invention, convergence of the SILCS FragMaps was facilitated by the inventors' selection of propane, benzene, and water as the "fragments," by the use of 1 M propane and 1 M benzene concentrations, and by combining results from 10 independent 5-ns SILCS MD simulations, as discussed above. The two-fold symmetry of the BCL-6 protein with its two symmetric binding sites and non-cooperative binding may allow for using two-fold symmetry in the FragMaps as a measure of convergence in accordance with the reality that convergence is never absolute. Analysis of the separate 5-ns simulations showed them to yield somewhat different FragMaps that did not clearly demonstrate two-fold symmetry (not shown); however, FragMaps generated as an ensemble average of all ten 5-ns simulations did exhibit the expected two-fold symmetry.

To visualize the extent of convergence, slices of the aliphatic carbon atom FragMap from propane along with the protein molecular surface were taken perpendicular to the two-fold symmetry axis of the protein. As shown in FIGS. 2A-D, these slices clearly demonstrate the expected two-fold symmetry in the FragMap, and hence, convergence. Similarly, as shown in FIGS. 3A-G and discussed below, converged results were seen for the aromatic carbon atom FragMap generated by mapping benzene carbon atoms and the hydrogen bond donor and acceptor FragMaps generated by mapping water molecules.

Figure 3C:
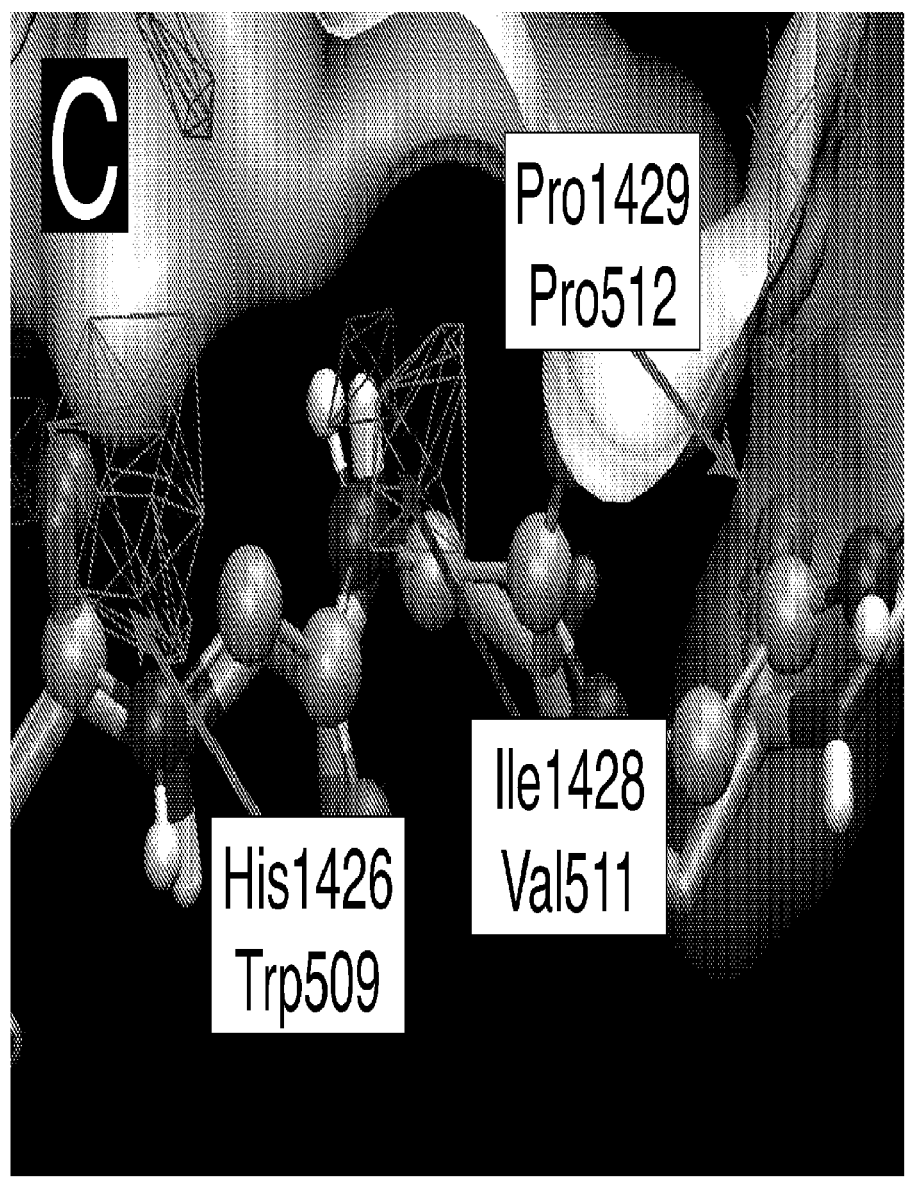

Fragmaps Identify Key Binding Interactions:

In an exemplary embodiment of the invention, SILCS FragMaps were compared with the crystal structures of the BCL-6:SMRT and BCL-6:BCOR complexes to validate the exemplary inventive method's ability to identify known binding interactions between the BCL-6 protein and the two bound peptide corepressors, SMRT and BCOR. FragMaps overlaid on the BCL-6:SMRT and BCL-6:BCOR structures are shown in FIGS. 3A-E: FIGS. 3A-C focus on interactions with the peptide backbones, while FIGS. 3D-E focus on the C-terminal regions of the peptides, which contain the majority of the thermodynamically important interactions between the peptides and BCL-6 protein. FragMap isosurfaces for hydrogen bond donors are in blue, hydrogen bond acceptors in red, aliphatic carbons in green, and aromatic carbons in purple, with the sites of discussion emphasized using arrows of the same color.

BCL-6 binding interactions conserved between the non-homologous SMRT and BCOR peptides were exclusively hydrogen bonding interactions with the peptide backbones, and the hydrogen bond donor and acceptor FragMaps showed these conserved interactions. As illustrated in FIG. 3A, starting from the N-termini of the two peptides, the backbones of SMRT Ala1416 and Val1418, and BCOR Ser499 and Ile501 act as hydrogen bond acceptors, and of SMRT Val1418 and Glu1420, and BCOR Ile501 and Ser503 as hydrogen bond donors, all of which were predicted by the high-probability regions of the corresponding FragMaps in an exemplary embodiment of the invention. As illustrated in FIG. 3B, toward the middle of the peptides, high-probability regions overlapped with SMRT Glu1420 and BCOR Ser503 as hydrogen bond acceptors to BCL-6, and SMRT Ser1424 and BCOR Ser507 as hydrogen-bond donors to BCL-6. Finally, as illustrated in FIG. 3C, at the C-termini, hydrogen-bond acceptor FragMap overlap was observed with SMRT His1426 and Pro1429 as well as BCOR Trp509 and Pro512, while hydrogen-bond donor FragMap overlap was seen for SMRT Ile1428 and BCOR Val511. The only peptide backbone hydrogen bonding interactions for SMRT not detected by SILCS were at the ends of the peptide, namely Ala1416 as a hydrogen bond donor and Ile1428 as a hydrogen bond acceptor, which may be explained by the high crystallographic temperature factors of these residues. In the case of the BCOR peptide, only the Ser508 backbone was not detected as a strong hydrogen bond donor. Thus, in eighteen out of twenty-one cases, high probability regions in the experimental SILCS FragMaps predicted the location of both SMRT and BCOR peptide backbone hydrogen bonds to BCL-6.

More interesting than the conserved backbone hydrogen bonds were the non-conserved interactions involving sidechains from the C-terminal ends of the two peptides. These C-terminal amino acids have large contact areas and buried surfaces, correlating with these residues contributing most strongly to the peptide binding affinities, as measured by competitive fluorescence polarization titrations involving SMRT or BCOR peptides that have single amino acid substitutions to either alanine for non-alanine residues or glycine for alanine residues. To be considered useful, the SILCS method should be capable of predicting these important interactions.

Figure 3D:
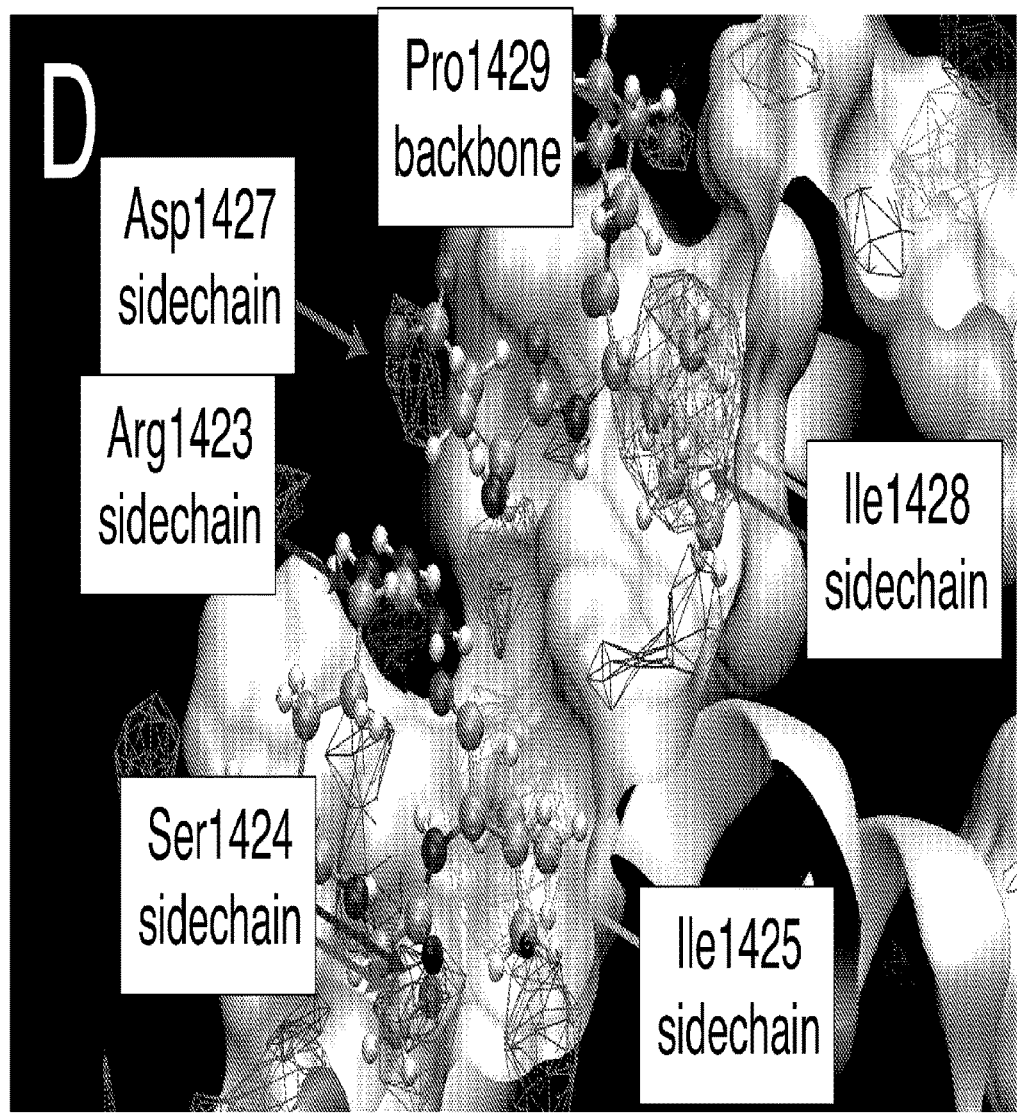

The SILCS FragMaps of an exemplary embodiment of the invention captured every one of the thermodynamically important C-terminal sidechain interactions of the SMRT peptide with BCL-6. In the SMRT peptide, Arg1423, Ser1424, Ile1425, Asp1427, Ile1428, and Pro1429 in the C-terminal half make large contributions to the binding affinity. Analysis of the crystal structures showed that the sidechains of Arg1423, Ser1424, and Asp1427 all formed hydrogen bonds to BCL-6, while both the Ile1425 and Ile1428 aliphatic sidechains were buried in hydrophobic pockets. As illustrated in FIG. 3D, high-probability regions in the hydrogen-bond donor FragMap overlapped with the polar hydrogens in the Arg1423 and Ser1424 sidechains, and high-probability regions in the hydrogen-bond acceptor FragMap overlapped with the oxygens in the Ser1424 and Asp1427 sidechains. As also illustrated in FIG. 3D, high-probability regions in the aliphatic carbon FragMap encompassed both the Ile1425 and Ile1428 sidechains. Interestingly, only the Ile1428 sidechain and not the Ile1425 sidechain was overlapped by a high-density region in the aromatic carbon FragMap. This suggests that the Ile1428 pocket can accommodate both aliphatic and aromatic carbons, while the Ile1425 pocket will preferentially bind only aliphatic carbons. Recent experimental evidence to this effect exists in the form of a crystal structure of BCL-6 with a small-molecule inhibitor, in which an aromatic moiety binds in the Ile1428 pocket. Such differentiation emphasizes the ability of the SILCS method of an exemplary embodiment of the invention to account for the subtle energetic contributions that dictate the binding of different classes of hydrophobic moieties.

Pro1429 is interesting in that it is the only amino acid in the C-terminal region of the SMRT peptide that makes a large thermodynamic contribution to binding, yet whose sidechain is not involved in an interaction with the BCL-6 protein. Rather, its backbone carbonyl acts as a hydrogen bond acceptor, and this interaction is indeed seen in the corresponding FragMaps of FIGS. 3C-D. This result indicates that Pro1429Ala mutation likely has a strong affect on the SMRT binding affinity due to an increase in conformational entropy and the fact that proline occupies the extended region of φ/ψ space while alanine preferentially occupies the helical region (Lovell S C, et al. (2003) Structure validation by $C_\alpha$ geometry: φ, ψ and $C_\beta$ deviation. *Proteins: Struct, Funct, Bioinf* 50:437-450). Such conformational effects are also suggested to lead to the lack of a FragMap density associated with the sidechain of Pro1429.

Figure 3E:
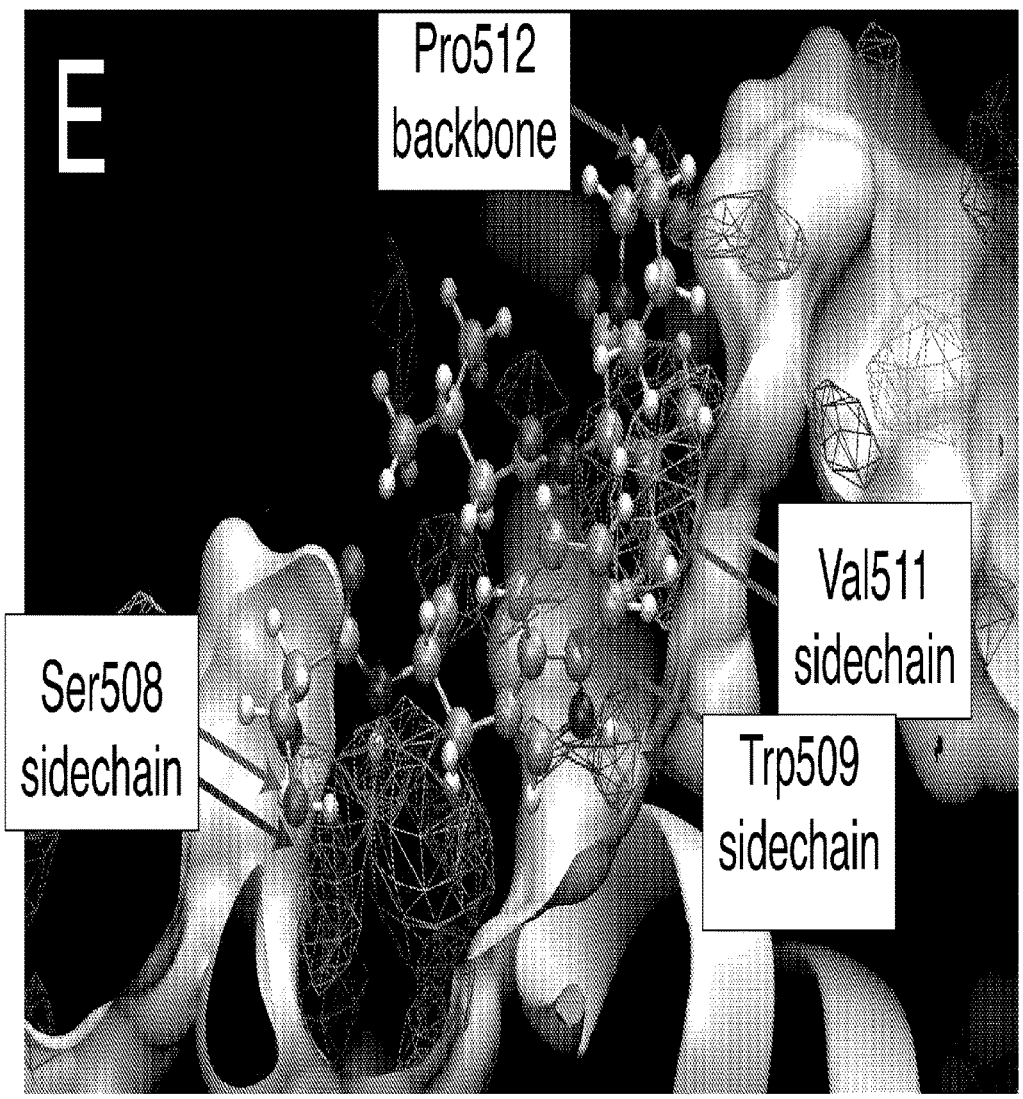

As illustrated in FIG. 3E, the SILCS FragMaps of an exemplary embodiment of the invention also captured the thermodynamically important interactions of the BCOR peptide C-terminal residues 508-512. These include sidechain interactions for Ser508, Trp509 and Val511. Surprisingly, no overlap was seen for the Val510 sidechain with a high-density region in either the aliphatic or aromatic FragMaps. This may have an explanation similar to that for SMRT Pro1429, in that the Val510Ala mutation may cause a decrease in binding affinity due to replacement of an amino acid that prefers an extended conformation with the helix-promoting alanine. Finally, as with the homologous SMRT Pro1429, the BCOR Pro512 backbone overlapped with a high-density region in the hydrogen bond acceptor FragMap while no sidechain overlap was seen, as illustrated in FIGS. 3C-E.

SILCS Captures Large Molecule Flexibility:

Because the SILCS simulations of an exemplary embodiment of the invention used all-atom explicit-solvent MD simulations, flexibility of a large molecule, for example, the BCL-6 oncoprotein, was included. As observed crystallographically, there are important differences in the conformations of BCL-6 sidechains in the peptide-binding groove between the BCL6 apo, BCL-6:SMRT and BCL-6:BCOR crystal structures. For example, as shown in FIGS. 4A-D, BCL-6 Arg24 sidechain dihedral angles had significantly different values in crystal structures of the unliganded protein, the BCL-6:SMRT complex, and the BCL-6:BCOR complex, while the BCL-6 His116 sidechain underwent a dramatic rearrangement between the SMRT and BCOR complexes. SILCS simulations of the invention seeded with a single BCL-6 structure captured this heterogeneity in both Arg24 and His116, and may therefore inform the design of corepressors targeting such flexible binding sites.

The SILCS MD behavior of the BCL-6 His116 sidechain is especially relevant because of the large experimentally-determined conformational change required in this sidechain for BCL-6 to accommodate both the SMRT and the BCOR peptides. The SILCS MD of an exemplary embodiment of the invention sampled both the His116 sidechain conformation observed in the BCL-6:SMRT crystal structure used to initiate all the SILCS simulations, and the very different conformation in the BCL-6:BCOR crystal structure, as illustrated in FIGS. 3F-G. In the SILCS MD, the His116 sidechain reversibly shifted between the initial, BCL-6:SMRT conformation (FIG. 3F, purple) and a second conformation. In this second conformation, His116 formed a hydrogen-bonding complex with a water molecule that acted as a hydrogen bond donor to the sidechain and as an acceptor to the His116 backbone (FIG. 3F, colored by atom type), a complex not possible in the initial conformation due to the location of the sidechain. Furthermore, as illustrated in FIG. 3G, this MD second conformation was the same as in the BCL-6:BCOR crystal structure and enabled hydrogen bonding between BCL-6 His116 and the BCOR Ser508 sidechain hydroxyl in the BCL-6:BCOR crystal structure. As illustrated in FIG. 3G, the Ser508 hydroxyl donated a hydrogen bond to the His116 sidechain and accepted a hydrogen bond from the His116 backbone amide NH group in the same manner as the water molecule in the simulation illustrated by FIG. 3F Importantly, the hydrogen bond donor and acceptor FragMaps showed that these are high-probability, i.e., favorable free energy, interactions.

An additional example of the ability of SILCS simulations of the invention to take into account protein flexibility exploits the experimental structures where the BCL-6 Arg24 sidechain dihedral angles have significantly different values in crystal structures of the unliganded protein, the BCL-6: SMRT complex, and the BCL-6:BCOR complex. Two BCL-6 Arg24 residues in the SILCS MD sample sidechain $\chi$ dihedral values were observed in the unliganded BCL-6 and the BCL-6:BCOR complex crystals, even though all SILCS simulations were seeded with the BCL-6:SMRT complex coordinates. This is demonstrated by $\chi$ dihedral distributions from the cumulative 50-ns of MD simulation, in which these sidechains sample conformations significantly differ from their starting seed conformations. As illustrated in FIGS. 4A-D, the heterogeneous sampling was true for all four $\chi$ angles, demonstrating SILCS ability to sample experimentally-relevant conformations that significantly differ from those in the initial conformation.

These results emphasized the ability of the SILCS method of an exemplary embodiment of the invention to include protein flexibility and the ability of the method to identify locations of favorable interaction sites on the protein surface that arise from protein flexibility. It should be emphasized that the conformational changes that SILCS may take into account are related to the timescales of the MD simulations and of the conformational changes themselves; the present results imply that readily-accessible timescales can account for biologically important sidechain conformational heterogeneity.

Application of SILCS to Optimization of a Low Molecular Weight Inhibitor:

SILCS simulations were undertaken to apply the SILCS method of an exemplary embodiment of the invention to the 57-6/BCL-6 complex, where 57-6 is an inhibitor known to bind to the BCL-6 protein (Cerchiettil L C, et al, "A small molecule inhibitor of BCL6 kills DLBCL cells in vitro and in vivo." Submitted for publication.). A SILCS MD simulation was performed starting from the 57-6/BCL-6 crystal structure with the acidic groups model built on the inhibitor. The simulation included thirteen fragment ligands that are analogs of amino acid sidechains at concentrations of approximately 100 mM and was extended for 100 ns. In parallel, a simulation of the thirteen fragment ligands in aqueous solution was undertaken to obtain the average voxel number counts in the absence of the protein.

Figure 5:
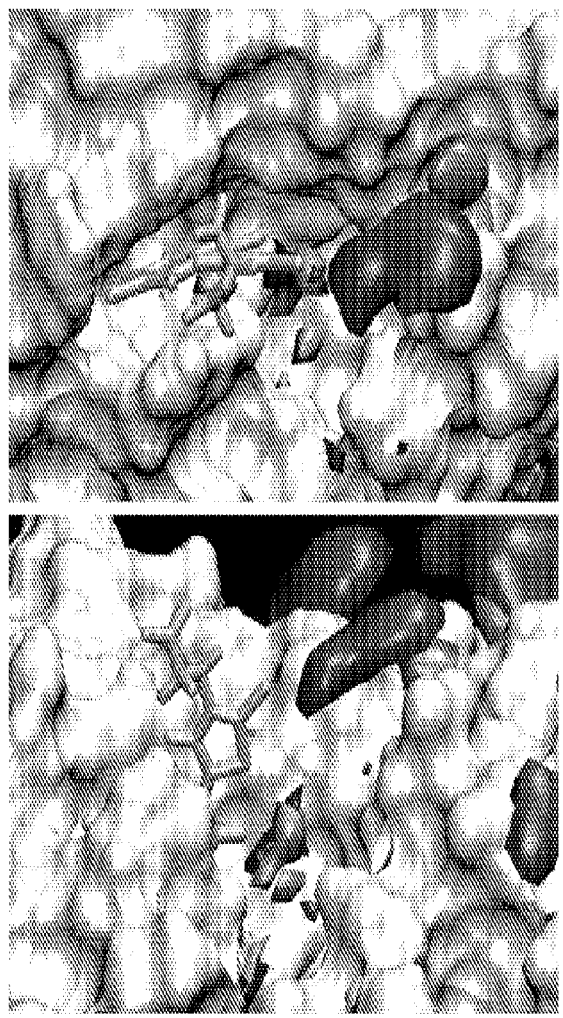
FIG. 5 illustrates a SILCS map of BCL-6 in the presence of a known BCL-6-binding small-molecule, 57-6, in which the surface of BCL-6 is white, 57-6 is pink and isosurface defining maps of functionalities are: amide C in green, amide N in red, amino N in purple, and benzene in brown, where the remaining isosurfaces including that of the amide 0 are omitted for clarity, and where the two views are a 90° rotation of the same image.

Analysis of the SILCS simulation in the presence of the 57-6 inhibitor was next undertaken to determine the utility of the SILCS approach for ligand optimization. From the 100 ns simulation, SILCS maps for atoms in the different fragments were calculated. Of the SILCS maps, selected isosurfaces are illustrated in FIG. 5, including those for the amide C (green), amide N (red), amino N (purple), and benzene C (brown) atoms, with the amide N and C maps located adjacent to both the 5-membered ring of the indoline and the central 5-membered sulfur containing heterocycle of the 57-6 inhibitor (note that the amide O isosurface has been omitted for clarity). These isosurfaces are located in an open region in the binding site, suggesting that addition of an amide moiety may facilitate binding.

Figure 6:
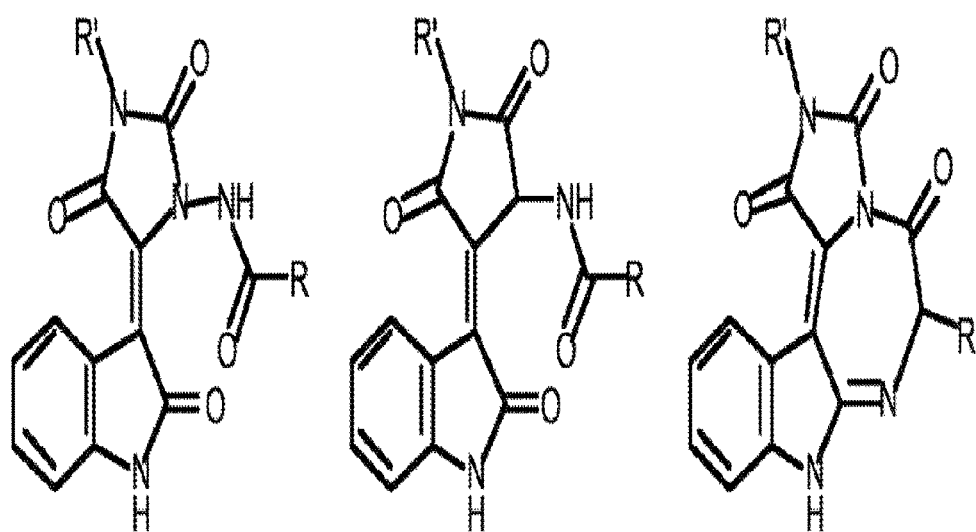
FIG. 6 illustrates binding small-molecule 57-6 analogs that were designed based on the SILC maps and synthetic considerations.

It was then undertaken to identify synthetically accessible chemical analogs of the 57-6 inhibitor that could exploit this information. From these efforts, the three chemical analogs illustrated in FIG. 6 were designed. These compounds include a modified central heterocycle designed to impart stability while placing an amide moiety in the region suggested by the SILCS maps. Steric overlap of amide with the oxygen on the indoline in the first two analogs motivated design of the cyclic analog on the right of FIG. 6.

Computer Aided Drug Design Optimization Based on a Two-Tier Approach Using SILCS:

In an exemplary embodiment of the invention, computer aided drug design (CADD) may be used to facilitate the drug discovery optimization process by a two-tier approach using SILCS: (1) suggesting possible modifications to synthetic chemists by using SILCS in the first tier and (2) evaluating the collection of modifications suggested by synthetic chemists for those modifications with the highest probability of improving binding affinity in the second tier.

SILCS maps may be generated by performing MD simulations of a complex of a large molecule, for example, the BCL-6 protein, and known bound ligand, such as, for example, the 57-6 inhibitor, initiated from x-ray structures or CADD models of the complex. SILCS simulations of an exemplary embodiment of the invention may be performed in two tiers. Tier one may involve a minimal set of chemical ligands to identify general classes of binding sites on the exemplary protein in the vicinity of the exemplary inhibitor that may indicate regions of the exemplary inhibitor appropriate for certain types of chemical modifications. Stage one ligands may, for example, include propane and benzene to identify sites amenable to aliphatic or aromatic groups, respectively, and may use water to identify sites appropriate fro hydrogen bond donors and acceptors.

Analysis of the initial tier one SILCS FragMaps may identify classes of functionalities to investigate in the tier two SILCS simulations. For example, if the tier one SILCS analysis indicates a hydrogen bond donor site adjacent to the exemplary inhibitor, then the tier two ligands may include any of a variety of molecules that include the functionality of a hydrogen bond donor, such as, for example, methanol, acetamide, imidazole, and pyrrole. Similarly, if an aliphatic functionality is indicated by the tier one analysis, the tier two ligands may include any of, for example, propane, butane, isobutane, and isopentane. In many case, it is anticipated that tier one SILCS analysis may identify sites appropriate for different types of functionalities, which are adjacent to one another, as illustrated in FIG. 3D, where, for example, a hydrogen bond donor region is directly adjacent to the region around the Ile428 sidechain of SMRT, which accommodates either an aliphatic or an aromatic group. In such a case, a tier two SILCS simulation may include ligands that contain both types of functionalities, for example, any of piperidine, piperazine, pyrrole, pyrrolidine, and indole. Results from the tier two SILCS simulation may yield detailed information on the types of functional groups, corresponding to the particular types of tier two ligands used, and their respective binding sites to possibly modify the known bound ligand to the large molecule for drug design. The results from the tier two SILCS simulation may be used by synthetic chemists in developing synthetic strategies for lead compound development.

The foregoing description of exemplary embodiments will so fully reveal the general nature of the invention that others can, by applying current knowledge, readily modify and/or adapt for various applications such embodiments without departing from the generic concept, and, therefore, such adaptations and modifications should and are intended to be comprehended with the meaning and range of equivalents of the disclosed exemplary embodiments. It is to be understood that the phraseology or terminology employed herein is for the purposes of description and not of limitation. Therefore, while the exemplary embodiments of the invention are described in terms of preferred embodiments, those skilled in the art will recognize that the embodiments of the invention can be practiced with modification within the spirit and scope of the appended claims.

What is claimed is:

1. A method for mapping an affinity pattern of a large molecule for small molecules or water molecules, said method carried out on a computer and comprising:
   initiating an explicit-solvent molecular dynamics simulation of a system comprising 3-D structures of a large molecule, water molecules, and at least two different small molecules, wherein the water molecules and small molecules are randomly distributed in the system, and wherein the 3-D structures do not overlap one another;
   simulating a competition
   (i) between the small molecules and
   (ii) between each of the small molecules and water molecules for binding to the large molecule;
   computing probability maps for the binding of each of the small molecules and water molecules to the large molecule; and
   using the probability maps to map an affinity pattern of the large molecule for the small molecules or water molecules;
   wherein the probability maps are computed by binning one or more atoms of the water molecules into voxels if the water molecules are within 2.5 Å of the large molecule, and binning the small molecules into voxels if the small molecules are within 5 Å of the large molecule.

2. The method of claim 1, wherein the large molecule is selected from the group consisting of DNA, RNA, carbohydrate, glycolipid, protein, glycoprotein, complex of protein and bound ligand, complex of glycoprotein and bound ligand, complex of DNA and bound ligand, complex of RNA and bound ligand, complex of carbohydrate and bound ligand, complex of glycolipid and bound ligand, and combination thereof.

3. The method of claim 1, wherein the small molecules comprise aliphatic molecules selected from propane, butane, isobutene, isopentane, or a combination thereof.

4. The method of claim 1, wherein the small molecules comprise aromatic molecules selected from benzene, imidazole, phenol, aniline, pyridine, pyrrole, or combination thereof.

5. The method of claim 1, wherein the small molecules comprise hydrogen bond donors selected from water hydrogen, hydroxyl, methanol, acetamide, imidazole, pyrrole, amide, or combination thereof.

6. The method of claim 1, wherein the small molecules comprise hydrogen bond acceptors selected from water oxygen, carbonyl, ether, acetone, formaldehyde, or combination thereof.

7. The method of claim 1, wherein the small molecules comprise dual functionality ligands selected from piperidine, piperazine, pyrrole, pyrrolidine, indole, methanol, phenol, imidazole, aniline, pyridine, acetone, or combination thereof.

8. The method of claim 1, wherein the system comprises a volumetric grid.

9. The method of claim 8, wherein the volumetric grid comprises grid points on which the water molecules and small molecules are randomly placed.

10. The method of claim 9, wherein the grid points have a spacing corresponding to concentrations of the small molecules sufficient for competitive saturation of the small molecule ligands.

11. The method of claim 10, wherein the concentrations are independently greater than 0.01 mM and less than 10 M.

12. The method of claim 1, wherein the molecular dynamics simulation comprises obtaining free energies of the interaction of small molecules with the large molecule.

13. The method of claim 1, further comprising providing a plurality of systems and initiating molecular dynamics simulations on the plurality of systems.

14. The method of claim 1, wherein the small molecules comprise non-polar portions, and the method further comprising introducing a repulsive energy between the non-polar portions to prevent non-polar aggregation.

15. The method of claim 1, wherein the small molecules comprise propane and benzene.

16. The method of claim 1, further comprising binning one or more atoms of the water molecules and small molecules into voxels to obtain binned atoms.

17. The method of claim 16, wherein the small molecules are selected from the group consisting of small aliphatic molecules, small aromatic molecules, hydrogen bond donors, hydrogen bond acceptors, dual-functionality ligands, and combinations thereof.

18. The method of claim 16, wherein the small molecules comprise one or more aliphatic small molecules and aromatic small molecules and wherein carbons of the aliphatic small molecules are binned as aliphatic carbons and carbons of the aromatic small molecules are binned as aromatic carbons.

19. The method of claim 16, wherein the binned atoms in one or more voxels are counted to obtain counted atoms.

20. The method of claim 19, further comprising preparing a 3-D histogram of the counted atoms.

21. The method of claim 19, further comprising
   initiating an explicit-solvent molecular dynamics simulation on the system in the absence of the large molecule, to obtain a baseline spatial distribution of the water molecules and small molecules in the absence of the large molecule;
   binning atoms of one or more of the water molecules and small molecule ligands obtained in the baseline spatial distribution into voxels;
   counting the binned atoms in the voxels obtained in the baseline spatial distribution; and
   dividing the counted atoms obtained in claim 19 by the counted atoms obtained in the baseline spatial distribution, to obtain ratios of corresponding atoms in corresponding voxels.

22. The method of claim 21, further comprising preparing a 3-D histogram of the ratios.

23. The method of claim 22, further comprising selecting and graphing an isosurface of the 3-D histogram.

24. The method of claim 21, wherein
the large molecule is a BCL-6 protein;
the two different small molecules are propane and benzene.

* * * * *